(12) United States Patent
Shpigelmacher et al.

(10) Patent No.: US 12,040,131 B2
(45) Date of Patent: Jul. 16, 2024

(54) MAGNETIC PROPULSION SYSTEM FOR MAGNETIC DEVICES

(71) Applicant: BIONAUT LABS LTD., Herzliya (IL)

(72) Inventors: Michael Shpigelmacher, Los Angeles, CA (US); Alexander Sromin, Ashdod (IL); John Caputo, Los Angeles, CA (US); Eran Oren, Tel Aviv (IL); Eli Van Cleve, Los Angeles, CA (US); Nadav Cohen, Haifa (IL); Amir Geron, Modi'in (IL); Dennis Seely, San Diego, CA (US); Alex Kiselyov, San Diego, CA (US)

(73) Assignee: BIONAUT LABS LTD.

( * ) Notice: Subject to any disclaimer, the term of this patent is extended or adjusted under 35 U.S.C. 154(b) by 414 days.

(21) Appl. No.: 17/291,078

(22) PCT Filed: Oct. 31, 2019

(86) PCT No.: PCT/US2019/059096
§ 371 (c)(1),
(2) Date: May 4, 2021

(87) PCT Pub. No.: WO2020/096855
PCT Pub. Date: May 14, 2020

(65) Prior Publication Data
US 2021/0407717 A1 Dec. 30, 2021

Related U.S. Application Data

(60) Provisional application No. 62/755,660, filed on Nov. 5, 2018.

(51) Int. Cl.
*H01F 7/02* (2006.01)
*H02K 41/03* (2006.01)

(52) U.S. Cl.
CPC ......... *H01F 7/0273* (2013.01); *H02K 41/031* (2013.01)

(58) Field of Classification Search
CPC ............................ H01F 7/0273; H02K 41/031
See application file for complete search history.

(56) References Cited

U.S. PATENT DOCUMENTS

| 6,876,284 B2 * | 4/2005 | Wright | H01F 7/066 335/229 |
| 10,539,644 B1 * | 1/2020 | Alarcon Herrera | A61B 5/062 |

(Continued)

FOREIGN PATENT DOCUMENTS

| EP | 2 196 131 | 6/2010 |
| EP | 2 923 629 | 9/2015 |

(Continued)

OTHER PUBLICATIONS

Extended EP Search Report dated Mar. 7, 2022 in respect of EP Patent Application No. 19833954.1.

(Continued)

*Primary Examiner* — Sisay G Tiku
(74) *Attorney, Agent, or Firm* — Mark S. Cohen; PEARL COHEN ZEDEK LATZER BARATZ LLP (57) ABSTRACT

This invention relates to apparatus for creating a magnetic field to propel a magnetic device within a diverse media including biological matrices, tissues, organs, animals and humans. In one embodiment, a cylindrical dual Halbach array provides a uniform magnetic field with a settable field direction. Another embodiment provides support and orientation apparatus for a controlled-gradient conical magnet to achieve a full 4π steradian solid angle coverage around the specimen.

1 Claim, 12 Drawing Sheets

(56) References Cited

U.S. PATENT DOCUMENTS

| | | |
|---|---|---|
| 2003/0181788 A1 | 9/2003 | Yokoi et al. |
| 2004/0066107 A1* | 4/2004 | Gery ................... H02K 49/106 310/114 |
| 2008/0097487 A1 | 4/2008 | Pool et al. |
| 2010/0217275 A1 | 8/2010 | Carmeli et al. |
| 2011/0215888 A1 | 9/2011 | Abbott et al. |
| 2012/0238796 A1 | 9/2012 | Conlon |
| 2013/0172672 A1 | 7/2013 | Iddan et al. |
| 2013/0245356 A1 | 9/2013 | Fernandez et al. |
| 2013/0289579 A1 | 10/2013 | Yeung et al. |
| 2013/0303847 A1* | 11/2013 | Sitti ...................... A61B 1/041 600/101 |
| 2014/0103765 A1* | 4/2014 | Post .................... H02K 49/102 310/103 |
| 2014/0111202 A1* | 4/2014 | Wald ................... G01R 33/383 324/309 |
| 2014/0187907 A1* | 7/2014 | Duan ..................... A61B 1/041 600/409 |
| 2014/0312716 A1* | 10/2014 | Hunter ............... H02K 41/0356 310/12.18 |
| 2015/0018615 A1* | 1/2015 | Duan ................. A61B 1/00006 600/109 |
| 2015/0177343 A1 | 6/2015 | Wald et al. |
| 2015/0374395 A1 | 12/2015 | Creighton |
| 2015/0380140 A1* | 12/2015 | Duan ................... H01F 7/0257 600/109 |
| 2018/0223481 A1* | 8/2018 | Dunham ................ B61B 13/08 |
| 2021/0052190 A1* | 2/2021 | Kiselyov ................ A61B 5/055 |
| 2021/0228298 A1* | 7/2021 | Qiu ....................... A61B 34/73 |

FOREIGN PATENT DOCUMENTS

| | | | | |
|---|---|---|---|---|
| EP | 3260259 B1 * | 9/2020 | ............. | B28B 1/007 |
| EP | 3411697 B1 * | 11/2021 | ............. | G01N 24/08 |
| JP | 2005-161052 A | 6/2005 | | |
| JP | 2013-108986 A | 6/2013 | | |
| JP | 2015-519175 T | 7/2015 | | |
| JP | 7429995 B2 * | 2/2024 | .......... | F16C 32/0427 |
| WO | WO-2007130634 A2 * | 11/2007 | ......... | A61B 1/00156 |
| WO | WO-2011029592 A1 * | 3/2011 | ............. | A61B 34/70 |
| WO | WO-2011/072060 | 6/2011 | | |
| WO | WO-2017134635 A1 * | 8/2017 | ............. | G01N 24/08 |
| WO | WO-2018108850 A1 * | 6/2018 | | |
| WO | WO-2018/187826 | 10/2018 | | |
| WO | WO-2018187826 A1 * | 10/2018 | ........... | G01R 33/383 |
| WO | WO-2019/005293 | 1/2019 | | |
| WO | WO-2019005293 A1 * | 1/2019 | ............. | A61B 10/02 |
| WO | WO-2019/213362 | 11/2019 | | |

OTHER PUBLICATIONS

Partial Supplementary Search Report dated Jul. 22, 2022 in respect of EP Patent App. No. 19881328.9.
Extended EP Search Report dated Oct. 25, 2022 in respect of EP Patent Application No. 19881328.9.
Office Action dated Aug. 9, 2022 in respect of JP Patent Application No. 2021-523489 (with English translation thereof).
International Search Report dated Oct. 7, 2019 in respect of PCT Int'l Application No. PCT/US2019/041309.
International Preliminary Report on Patentability dated Jan. 21, 2021 in respect of PCT Int'l Application No. PCT/US2019/041309.
International Preliminary Report on Patentability dated May 20, 2021 in respect of PCT Int'l Application No. PCT/US2019/059096.
Joshi, et al., "Circular Halbach array for fast magnetic separation of hyaluronan-expressing tissue progenitors", Anal Chem. 2015, 87(19): pp. 9908-9915.
International Search Report dated Mar. 18, 2020 from corresponding International Patent Application No. PCT/US19/59096.

* cited by examiner

MAGNETIC PROPULSION SYSTEM FOR MAGNETIC DEVICES

CROSS-REFERENCE TO RELATED APPLICATIONS

This application is a U.S. national stage application under 37 U.S.C. 371 of PCT International Application PCT/US2019/059096, filed Oct. 31, 2019, which claims benefit of U.S. Provisional Application No. 62/755,660 filed Nov. 5, 2018, the priority dates of which are hereby claimed, and the contents of each of which are hereby incorporated by reference in their entireties.

FIELD

This invention relates to apparatus for creating a magnetic field to externally propel a magnetic device within a matrix of material, such as a viscous medium in a biological tissue.

BACKGROUND

In many medical applications, it can be useful to have a miniaturized mobile device (herein denoted as a "bot") to move in a medium such as found in a biological organism. For example, it may be desirable to move an internal device through tissue to a particular anatomic location to release a drug, gather diagnostic data, or conduct a remote-controlled surgical procedure. To facilitate such movement, propulsion and navigation utilizing magnetic fields has been developed.

One mode of propulsion involves applying an external uniform rotating magnetic field on internal device located inside the body. According to this mode, the internal device has a helical or a related shape (screw-like) exhibiting asymmetry and it comprises an embedded magnet with diametric magnetization. Rotating the external field exerts congruent rotational torque on the device, propelling it forward (like a screw). It is expected that reversing the external rotational field direction will yield a respective reverse particle dynamics. This propulsion method is denoted as "rotation."

Another propulsion mode involves applying an external non-uniform magnetic field (a "magnetic gradient") performing increasing strength along a controllable line (a "gradient line") to an internal device located inside the body. The device includes an embedded magnet or a metallic component. In response to the external field gradient, the device moves along the gradient lines generated by the external magnet. This propulsion method is denoted as "gradient-based motion."

A combination of the two above propulsion techniques are required to properly propel the bot through the tissue as each propulsion mode impacts the bot differently.

It is worth noting that the same magnetic system can be used to control other types of functionality of the bot remotely using a combination of magnetic field rotation and/or magnetic gradient, applied at a predefined time at a particular configuration, in parallel or separately from the propulsion of the bot. For example, in one embodiment the bot may contain an internal magneto-mechanic mechanism which extrudes a particular payload to the surrounding matrix in response to a predefined magnetic gradient or a predefined rotation of the external magnetic field generated by the magnetic system.

SUMMARY

Various embodiments of the present invention provide external apparatus that establishes a variable magnetic field to manipulate a bot, for example, to propel a bot through a matrix of interest or to expel or deliver a payload from the bot into a matrix of interest. Such a matrix of interest includes, but is not limited to, a media, extracellular matrix, a compartment, tissue, organ, blood, lymph, biliary or cerebrospinal fluid in the region of the magnetic field.

The term "magnet" herein denotes any object having a magnetic field. In particular, a combination of individual magnets, including an "array" of individual magnets is herein itself considered a "magnet". In some descriptions herein, a distinction is made between an "individual magnet" and an "array of magnets", but it is understood that an "array of magnets" is also considered to be a "magnet".

The term "propel" herein denotes the causing of any kind of physical motion, including, but not limited to: rotation, translation, vibration, oscillation, and combinations thereof.

The term "creating and manipulating a magnetic field" herein denotes making any changes to a magnetic field in a region, including, but not limited to: introducing a magnetic field into the region; moving a magnetic field from one place to another; and varying the intensity, flux, direction, and/or polarity of a magnetic field in the region.

According to certain embodiments, the external apparatus includes features such as:

a permanent field magnet;

multiple permanent field magnets;

an array of permanent field magnets arranged in a particular topological fashion to meet requirements such as: a specific field strength, field gradient/directionality as a function of distance, and trajectory away from the array.

An array of magnet may also include electromagnets which may or may not be composed of copper, aluminum or superconducting material exemplified by but not limited to NbTi.

An array according to a related embodiment is affixed, directly or indirectly, to a structural member, including but not limited to a platform, support, bracket, orienting apparatus, disk or other defined surface.

In another related embodiment, the magnet or array of magnets is attached to a mobility device having a motor to provide motion of the magnet or array, non-limiting examples of such motion including: rotation, cyclic motion (angular regular or irregular "rocking"; translational oscillation; and other such motion); vibration; trajectory motion (such as orbitally-circling a region); and combinations thereof.

As noted previously, a device according to various embodiments of the invention moves a bot via a torque, a linear force, and/or combinations thereof, wherein the torques and linear forces are applied via a magnetic field established by permanent magnets and arrays and/or electromagnets which are prepared and arranged as disclosed herein.

According to certain embodiments, the function of torque applied to a bot is to overcome friction of the bot against surrounding media (such as diverse matrices, biological tissues and compartments) or other propulsion resistance forces, while the linear force propels the bot through the media itself. A rotating magnetic field perpendicular to the direction of bot motion provides torque on the bot, while a controlled gradient of that same field amplitude along the direction of desired bot motion, provides a linear attractive force on the bot.

According to an embodiment of the present invention, there is provided a system for creating and manipulating a magnetic field to propel a magnetic device in a specimen, the system comprising: (a) a cylindrically-disposed plurality of rod shaped or related magnets enclosing a hollow space to include the analyte, matrix, subject or specimen of interest, each rod magnet thereof having a transverse magnetization; (b) wherein the plurality of rod shaped or related magnets form an array including but not limited to a Halbach array which includes: (c) a first array of rod magnets; and (d) a second array of rod magnets; (e) wherein the first array of rod magnets and the second array of rod magnets are interleaved in an alternating fashion such that magnets from the first array always have magnets from the second array as their nearest neighbors; (f) and could be manipulated to: (g) alter positioning of all the magnets of the first array; and (h) alter positioning of all the magnets of the second array; (i) wherein the dynamics of the magnets of the first array is independent of the dynamics of the magnets of the second array.

In addition, according to another embodiment of the present invention, there is further provided a device for creating and manipulating a magnetic field to propel a magnetic device in a specimen including but not limited to an ex vivo matrix, biological specimen as exemplified by blood, lymph, bile, spinocerebral fluid, tissue, organ or compartment, the device comprising: (a) a magnet for creating the magnetic field; (b) a stage for holding the specimen; (c) support and orienting apparatus for the magnet, to which the magnet is attached; (d) support and orienting apparatus for the stage, to which the stage is attached; and (e) at least one positioning drive apparatus containing a motor; (f) controlling mechanism, wherein: (g) the support and orienting apparatus for the magnet includes at least a first rotatable offset bracket; and (h) the support and orienting apparatus for the stage includes at least a second rotatable offset bracket; (i) wherein the second rotatable offset bracket is rotated according to a position of the first rotatable offset bracket, so as to allow the first rotatable offset bracket to rotate to any angular position without having the magnet blocked by the second rotatable offset bracket, (j) such that the system is operative to orient the magnet over a solid angle of $4\pi$ steradians with respect to the stage.

In addition, so far as the embodiment of the previous device, in which the stage holding the specimen may also be placed inside the magnet and the magnet may therefore be rotated $4\pi$ steradians with respect to the stage.

The current embodiments of the invention have the current advantages: (a) Gradient to mediate reliable, reproducible motion at considerable distances, (b) Versatility in a combination with mechanical component: 2D/3D options, (c) Feasible size, safety, modular nature, applicability to studies of diverse matrices including animals, (c) Ability to accommodate i) diverse particles, ii) imaging, iii) delivery and retraction, iv) other (micro)devices used in (micro) manipulation including microsurgery, (d) Facile integration into a platform along with other modules.

BRIEF DESCRIPTION OF THE DRAWINGS

The subject matter regarded as the invention is particularly pointed out and distinctly claimed herein. Embodiments of the invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Figure 1A:
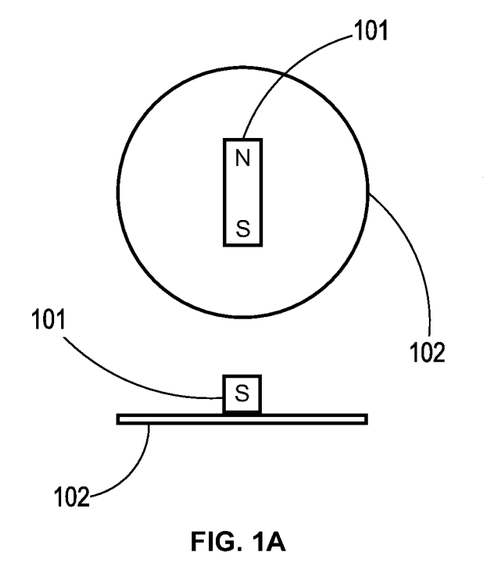
FIG. 1A illustrates a magnet on a yoke, according to an embodiment of the invention.
Figure 1B:
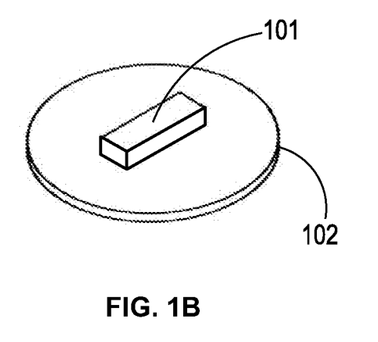
FIG. 1B is an isometric view of the magnet on a yoke of FIG. 1A.

FIG. 1A illustrates a permanent bar magnet 101 mounted on a disk-shaped ferromagnetic yoke 102 according to an embodiment of the invention. In related embodiments, yoke 102 takes other shapes. According to further embodiments of the invention, yoke material is steel. In still other embodiments, bar magnet 101 is a stack of individual magnets. FIG. 1B shows an isometric view of bar magnet 101 on yoke 102.

Figure 2:
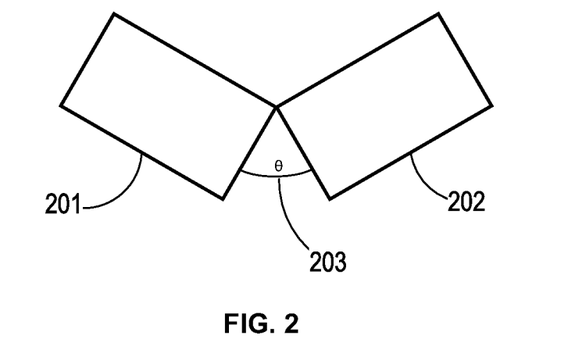
FIG. 2 illustrates a pair of similar magnets having a predetermined angular displacement, according to an embodiment of the invention.

FIG. 2 illustrates a magnet 201 in proximity to a similar magnet 202, wherein the two magnets have a predetermined angular displacement θ 203. In a related embodiment, the angular displacement θ is 60°, which in some cases maximizes the field strength for magnets of a given weight and composition.

Figure 3:
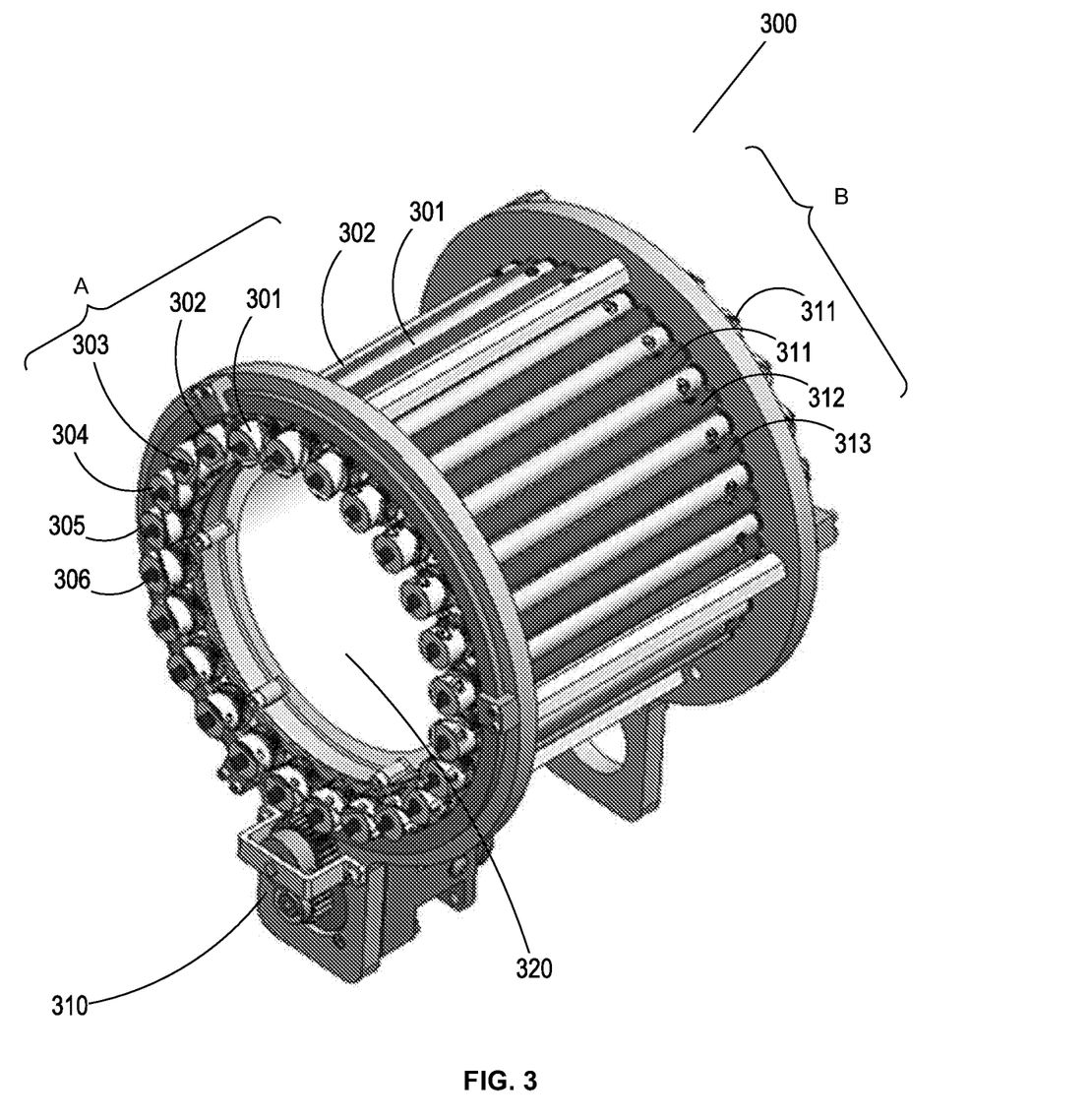
FIG. 3 illustrates a cylindrical arrangement of Halbach arrays, with a dual independent synchronizing mechanism, according to an embodiment of the present invention.

FIG. 3 illustrates a cylindrical arrangement 300 of Halbach arrays, with a dual independent synchronizing mechanism, according to an embodiment of the present invention, to make and use a system for creating and manipulating a magnetic field to propel a magnetic device in a specimen. In this embodiment, arrangement 300 has two independent Halbach arrays, herein denoted as array A and array B, respectively. Each element of a Halbach array is in the form of a rod shaped or alternative magnet having a transverse magnetization, so that rotating a magnet changes the direction of its magnetic field. The term "rod magnet having a transverse magnetization" herein denotes a rod-shaped or related magnet, being a cylinder like object whose length is greater than its diameter, and whose magnetic field lines lie substantially in planes orthogonal to the axis of the said cylinder, such that the poles of the magnet are on the curved exterior surfaces of the cylinder. The magnets are cylindrically-disposed to enclose a hollow space 320, which can accommodate a specimen treated with a nano or micro device featuring magnetic properties. The magnets of the two arrays are interleaved, as shown for two representative samplings in FIG. 3. Rod or rod like magnets 301, 302, 303, 304, 305, and 306 belong to array A, whereas rod or rod like magnets 311, 312, and 313 belong to array B, and the two arrays are interleaved, such that every magnet of array A lies between two magnets of array B, and every magnet of array B lies between two magnets of array A. In FIG. 3, array A magnets are shown as light-colored, whereas array B magnets are shown as dark colored. For the sake of illustration, a motor drive 310 moves the gears that rotate all array A magnets simultaneously, and independently rotate all array B magnets in a related fashion, for example simultaneously. The gear drives for array B are on the back side of Halbach array 300, and are related in construction to those of array A, which are visualized in FIG. 3. The Halbach array of FIG. 3 establishes a relatively uniform field in internal space 320.

Figure 4:
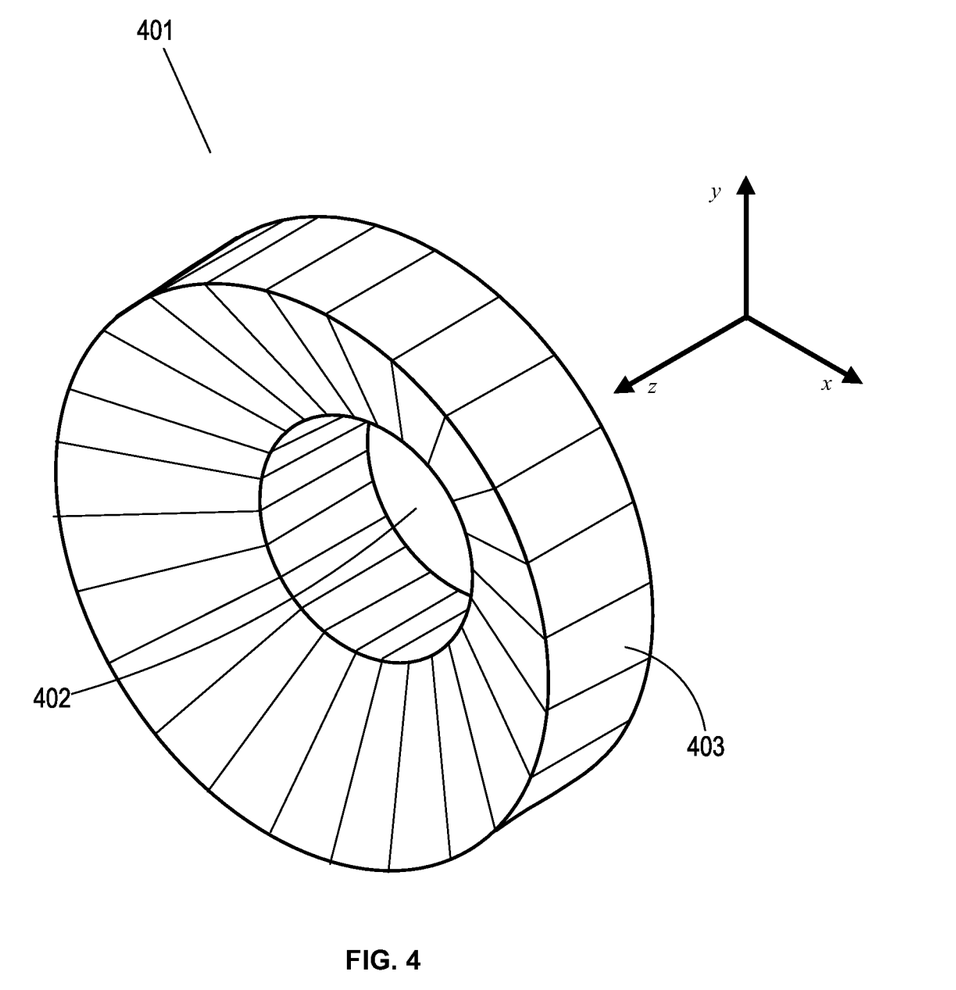
FIG. 4 is an isometric view of a conical magnet according to an embodiment of the present invention.

FIG. 4 illustrates a conical magnet 401 with a hollow internal space 402, according to an embodiment of the invention. In a related embodiment, conical magnet 401 is made of individual segments, one of which is shown as a segment 403. According to these embodiments, magnet 401 is characterized by a 3-dimensional gradient, and specimens can be placed inside of the resulting hollow internal space 402.

One of the key features provided by embodiments of the present invention is the ability to position magnet 401 at any desired location around a specimen, and to move magnet 401 continuously in any trajectory from that location to any other location. Mathematically, this requires being able to move magnet 401 continuously over a complete solid angle of 4π steradians. The described dynamics is accomplished by the apparatus shown in FIGS. 5A, and 5B; and illustrated in different arrangements providing 4π steradian coverage in FIG. 6A through FIG. 6G. In related embodiments of the invention, motion over the 4π steradian range includes cyclic motion, rocking, vibration, oscillation, and other repetitive movement.

In the following description, a system for positioning and orienting a magnet to propel a magnetic device in a specimen is described and illustrated for clarity in the specific case of a conical magnet. It is understood that this is a non-limiting example; in related embodiments, the same apparatus is used to position and orient other magnetic devices, including, but not limited to magnets of other shapes and having other field distributions, and arrays of magnets.

It is also contemplated that devices with a magnetic component for use in systems according to embodiments of the present invention will include devices described in International Patent Application PCT/US2018/030960 filed on May 3, 2018 and titled "METHODS AND SYSTEMS TO CONTROL PARTICLES AND IMPLANTABLE DEVICES," which is hereby incorporated by reference in its entirety. Briefly, such devices with a magnetic component are microelectromechanical (MEM) devices, which comprise: (i) an actuator; (ii) a responsive element; (iii) a sensor; and (iv) an electronic circuit; wherein: said actuator controls and operates said responsive element; said electronic circuit controls said actuator; and said sensor receives signals transmitted by a remote unit. It is also contemplated that systems according to embodiments of the present invention will be included in the platforms described in International Patent Application PCT/US2018/030960. Briefly, such platforms comprise the following modules: (a) one or more devices with a magnetic component and comprising embedded logic and various MEM components; (b) a delivery and/or retraction module, configured to deliver and/or retract the devices; (c) an external signal generator; (d) an imaging module, configured to monitor said particles; and (e) an integration module configured to receive inputs from and to provide output control commands to other modules; wherein: said modules are configured to interact/communicate with each other; and said modules are internally controlled, externally controlled or both; and wherein said platform provides active, pre-determined, fully controlled, precise delivery of said devices in vitro, in vivo, and/or in a patient.

Figures 5A, 5B:
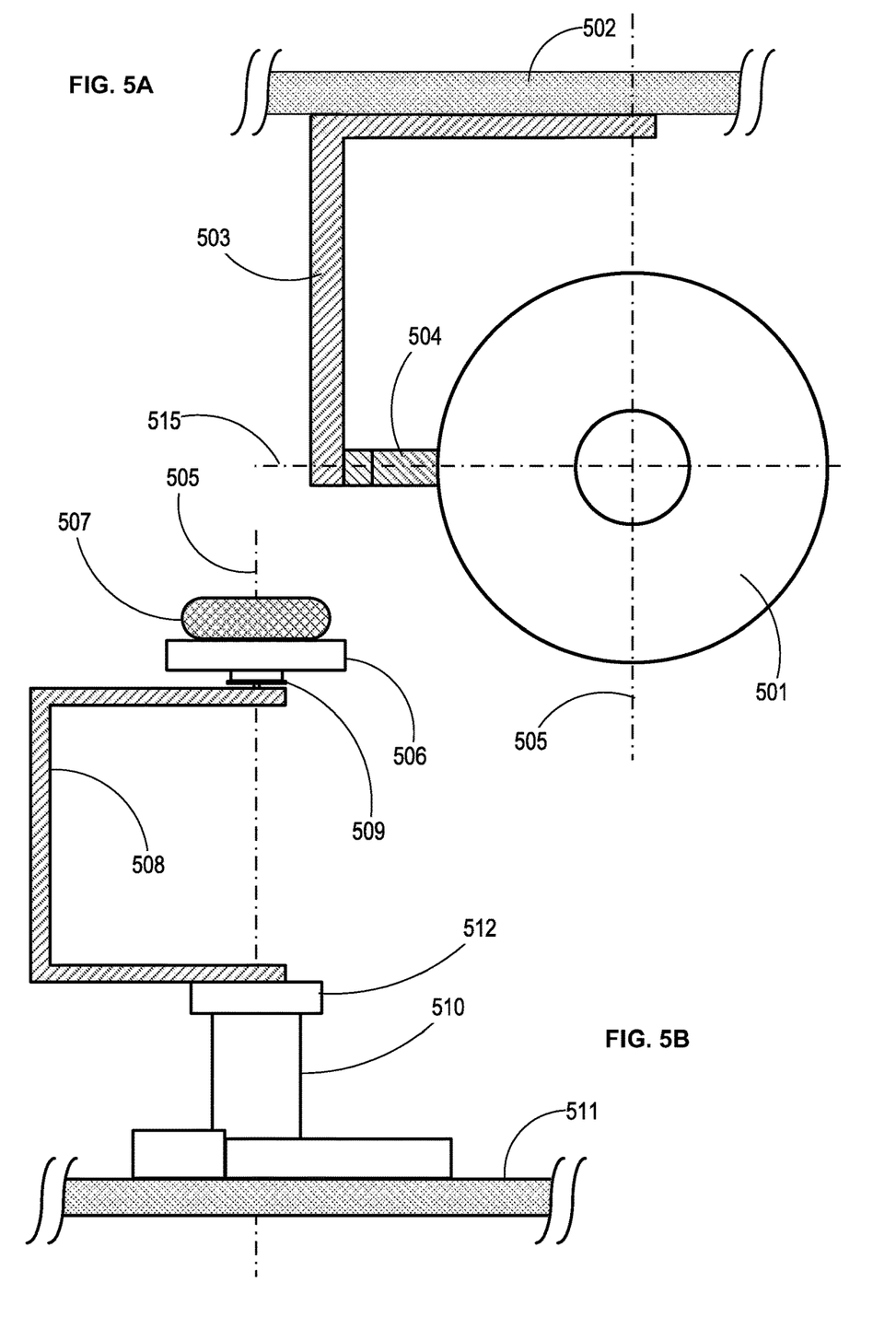
FIG. 5A illustrates a support mounting and orienting apparatus for the conical magnet of FIG. 4, according to an embodiment of the present invention.
FIG. 5B illustrates a stage for a specimen under investigation (SUI), and accompanying support and positioning apparatus, according to an embodiment of the present invention, for use with the conical magnet and support mounting and orienting apparatus of FIG. 5A.

FIG. 5A illustrates a support mounting and orienting apparatus for a conical magnet 501, according to an embodiment of the present invention. An upper structural member 502 supports the entire weight of the apparatus and provides stability for the elements that hang from it. A rotatable offset bracket 503 pivots around a vertical axis 505. The pivoting of offset bracket 503 is provided by a positioning drive apparatus containing a motor (not shown), which is able to rotate offset bracket 503 around a vertical axis 505 to any desired angular position. Attached to offset bracket 503 is another rotatable offset bracket 504 which supports magnet 501 and pivots around a horizontal axis 515 to any desired angular position. The pivoting of rotatable offset bracket 504 is provided by another positioning drive apparatus containing a motor (not shown), which is able to rotate offset bracket 504 around horizontal axis 515 to any desired angular position.

FIG. 5B illustrates a support and positioning apparatus for a stage 506 upon which is placed a specimen under investigation (SUI) 507. A rotatable offset bracket 508 supports stage 506. Offset bracket 508 is attached to and supported by a plinth 512, which is rotated by a positioning drive apparatus 510 containing a motor, which is able to rotate offset bracket 508 to any desired angle around vertical axis 505. This is the same vertical axis 505 around which offset bracket 503 is rotated. That is, during operation, the apparatus of FIG. 5A is precisely aligned with the apparatus of FIG. 5B, such that offset brackets 503 and 508 both rotate simultaneously around vertical axis 505. A freely-rotating connector 509 maintains a stationary angular orientation of stage 506 as offset bracket 508 rotates. The apparatus of FIG. 5B is supported and stabilized by a lower structural member 511.

According to various embodiments of the present invention, offset brackets 503 and 508 provide support that is offset from vertical axis 505, and offset bracket 504 provides support that is offset from horizontal axis 515. This enables magnet 501 to be positioned directly in-line along both vertical axis 505 and horizontal axis 515, without interference from any supporting members that would block magnet 501 from being positioned as desired. In this manner, magnet 501 covers the full 4π steradian solid angle surrounding the specimen. According to these embodiments, the 4π steradian solid angle coverage is readily achieved by rotating offset bracket 508 so that it is always oriented 180° opposite to the rotated angular position of offset bracket 503. Meeting this orientation constraint guarantees that offset bracket 504 (to which magnet 501 is directly affixed) can be rotated to any angle around horizontal axis 515 without having magnet 501 blocked by offset bracket 508. In certain embodiments of the invention, offset bracket 508 is continuously rotated synchronously with respect to offset bracket 503 so that the above orientation constraint is always met; in other embodiments, however, offset bracket 508 is rotated only when necessary to avoid blocking magnet 501 by offset bracket 508.

The combination of magnet 501 with the above apparatus constitutes a system for creating and manipulating a magnetic field to propel a magnetic device in a specimen. The following discussion and drawings illustrate how such a combination can be constructed and used.

FIG. 6A through FIG. 6G illustrate how magnet 501 can be positioned to six polar positions—two on each of the three coordinate axes (i.e., ±x, ±y, ±z). Note that there are multiple configurations that position magnet 501 in the same location. For example, FIG. 6C and FIG. 6F both position magnet 501 in the same location relative to the specimen, but with different but equivalent configurations. These polar positions are special cases, but it can readily be seen that this apparatus is capable of moving magnet 501 into any position relative to stage 506, over a complete solid angle of 4π steradians That is, in spherical coordinates r, θ, and φ, apparatus according to these embodiments of the invention can position magnet 501 for any angular values of θ and φ. According to certain embodiments, r is constant—and this condition is illustrated in FIG. 6A through FIG. 6G. In further embodiments, however, r can be varied somewhat by changing one or more of the x, y, z coordinates of stage 506, and in related embodiments this is accomplished by including x-y-z control into the apparatus, non-limiting examples of which include introducing x-y-z control into the positioning of stage 506 and/or the positioning of plinth 512.

Figure 6A:
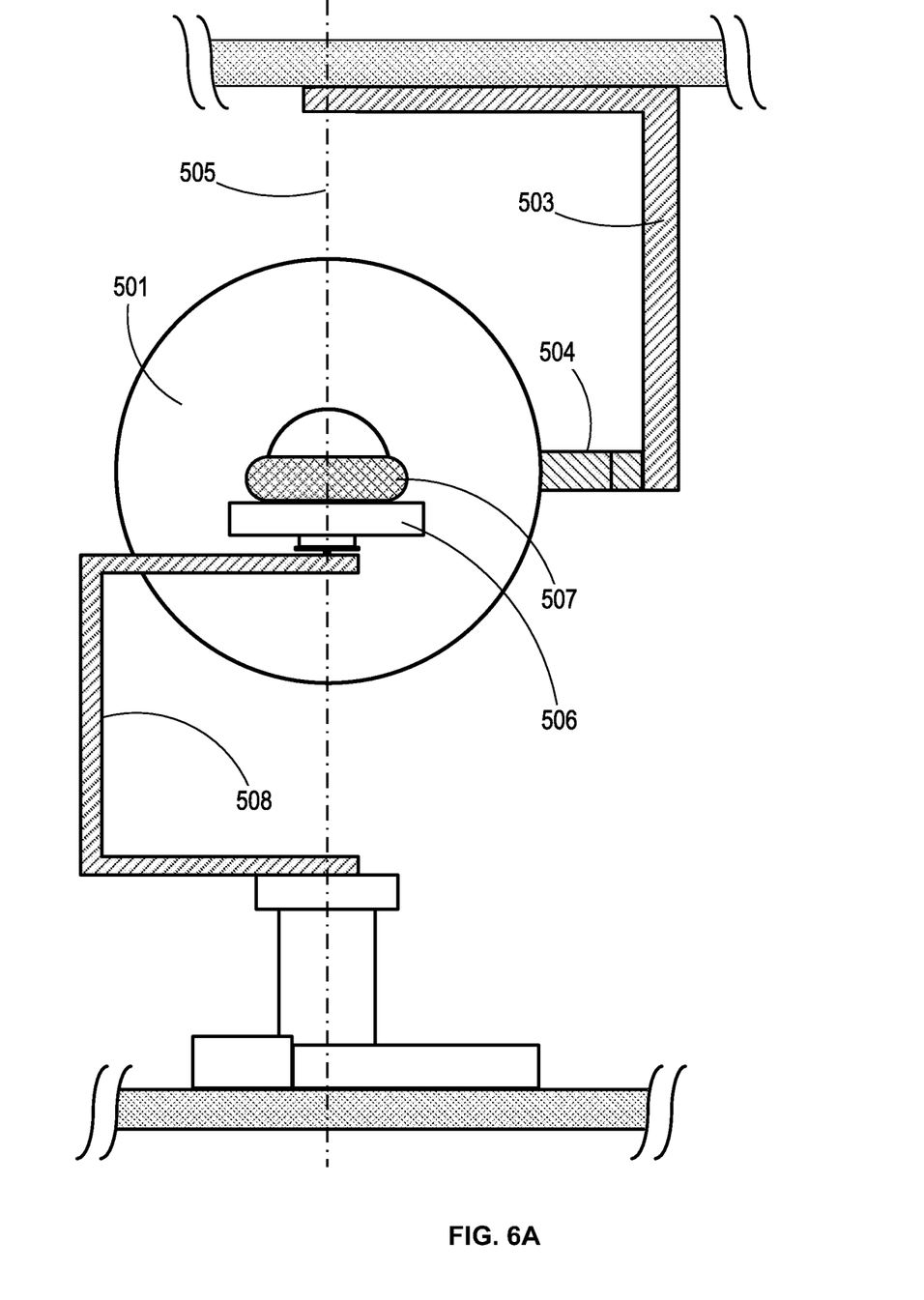
FIG. 6A illustrates the conical magnet support mounting and orienting apparatus of FIG. 5A in conjunction with the SUI stage and support and positioning apparatus of FIG. 5B, with the conical magnet oriented behind the SUI, according to an embodiment of the invention.

FIG. 6A illustrates magnet 501 with the support mounting and orienting apparatus of FIG. 5A in conjunction with SUI stage 506 and support and positioning apparatus of FIG. 5B, with conical magnet 501 oriented behind the SUI, according to an embodiment of the invention.

Figure 6B:
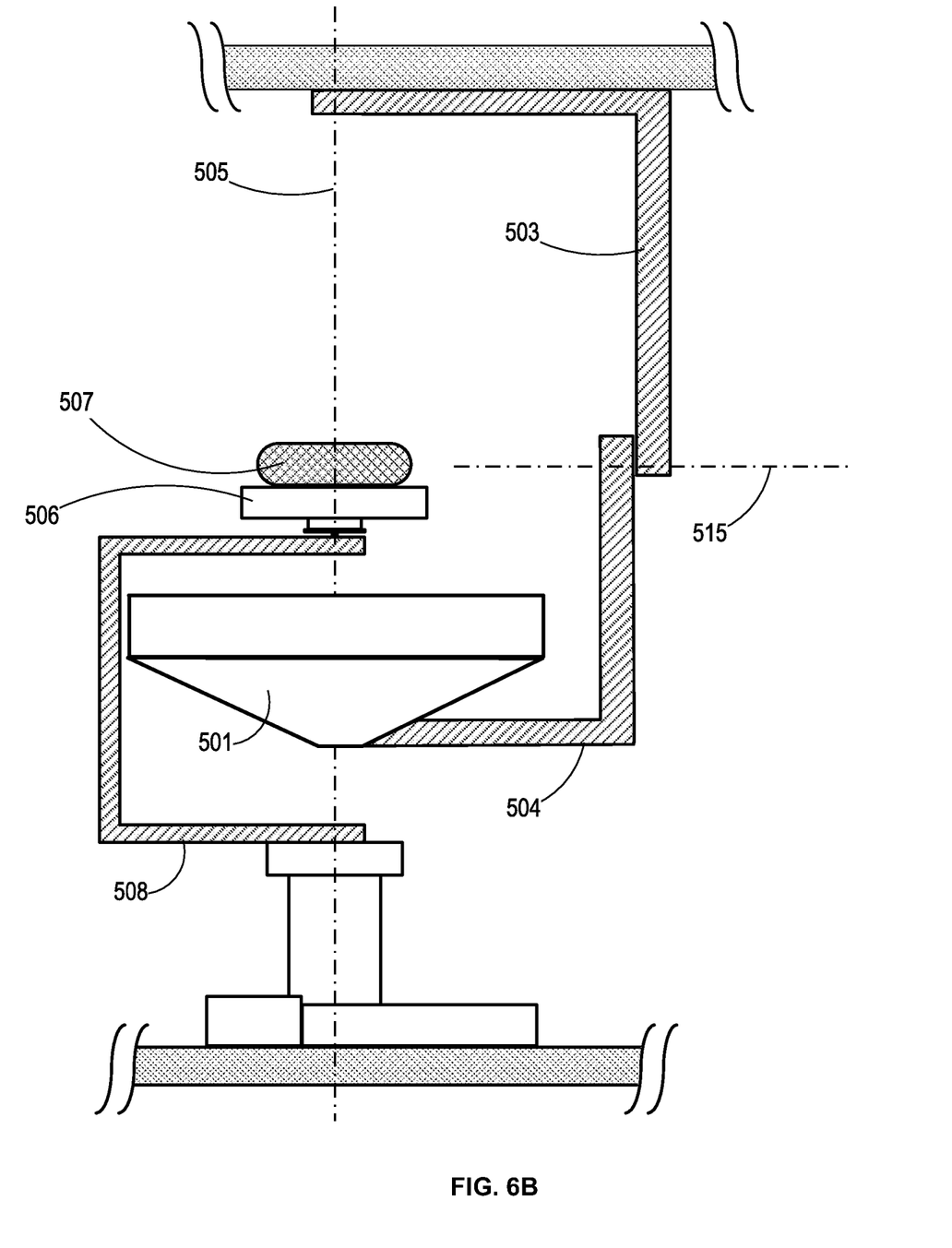
FIG. 6B illustrates the configuration of FIG. 6A as arranged with the conical magnet oriented below the SUI, according to an embodiment of the invention.

FIG. 6B illustrates magnet 501 with the support mounting and orienting apparatus of FIG. 5A in conjunction with SUI stage 506 and support and positioning apparatus of FIG. 5B, with conical magnet 501 oriented below the SUI, according to an embodiment of the invention.

Figure 6C:
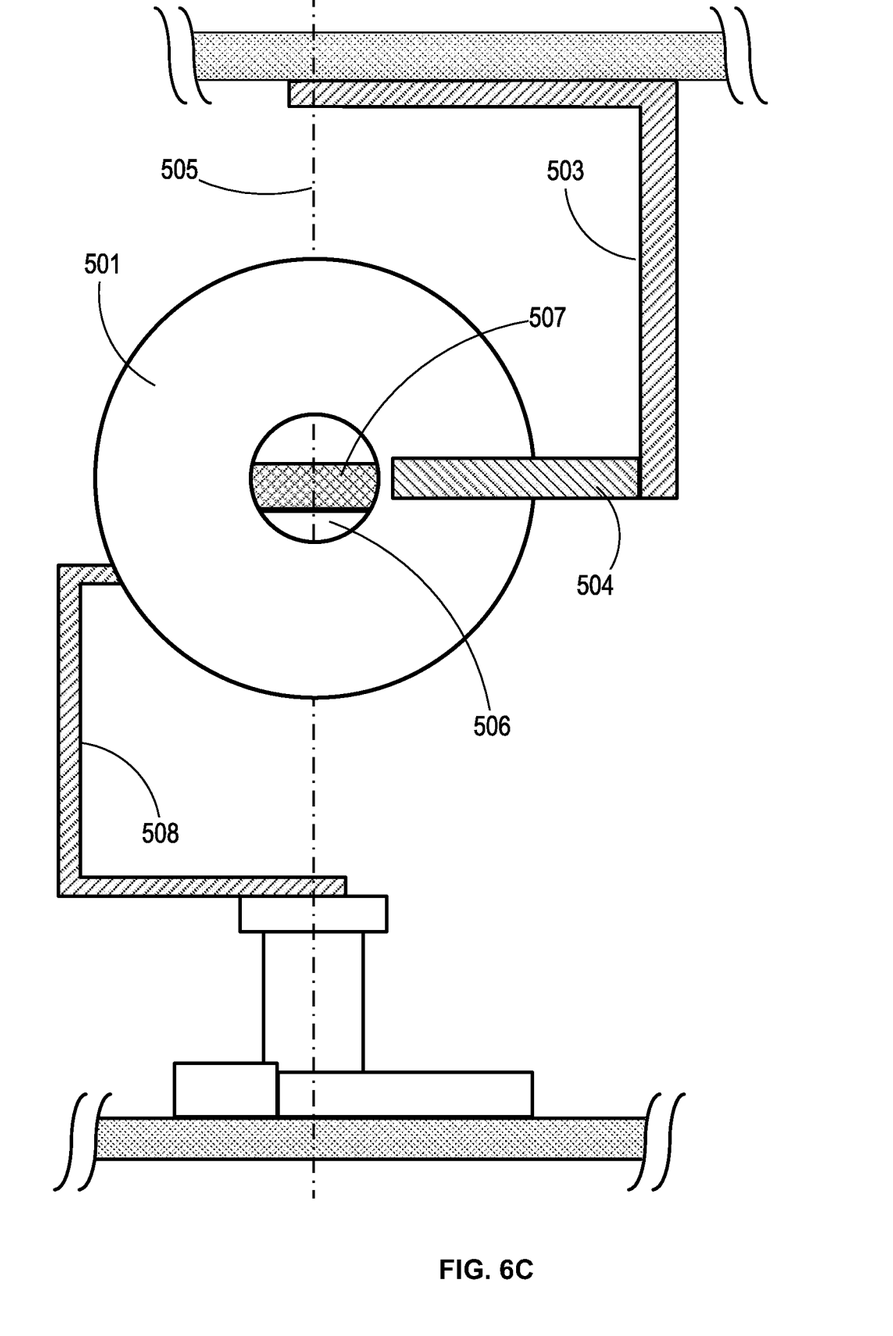
FIG. 6C illustrates the configuration of FIG. 6A as arranged with the conical magnet oriented in front of the SUI, according to an embodiment of the invention.

FIG. 6C illustrates magnet 501 with the support mounting and orienting apparatus of FIG. 5A in conjunction with SUI stage 506 and support and positioning apparatus of FIG. 5B, with conical magnet 501 oriented in front of the SUI, according to an embodiment of the invention. Compare with FIG. 6F, as described below, in light of the remarks above concerning multiple configurations for achieving the same orientation of magnet 501.

Figure 6D:
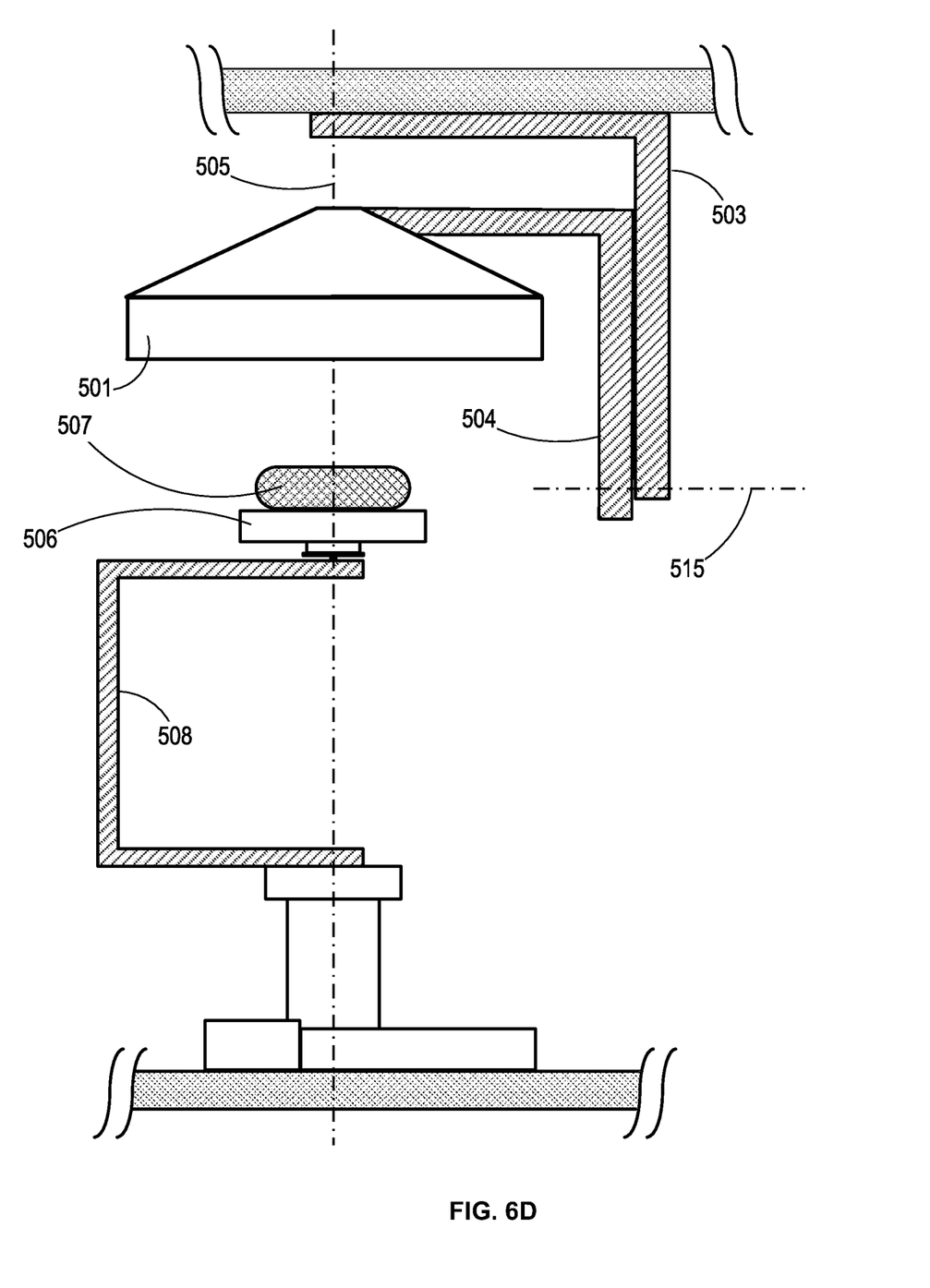
FIG. 6D illustrates the configuration of FIG. 6A as arranged with the conical magnet oriented above the SUI, according to an embodiment of the invention.

FIG. 6D illustrates magnet 501 with the support mounting and orienting apparatus of FIG. 5A in conjunction with SUI stage 506 and support and positioning apparatus of FIG. 5B, with conical magnet 501 oriented above the SUI, according to an embodiment of the invention.

Figure 6E:
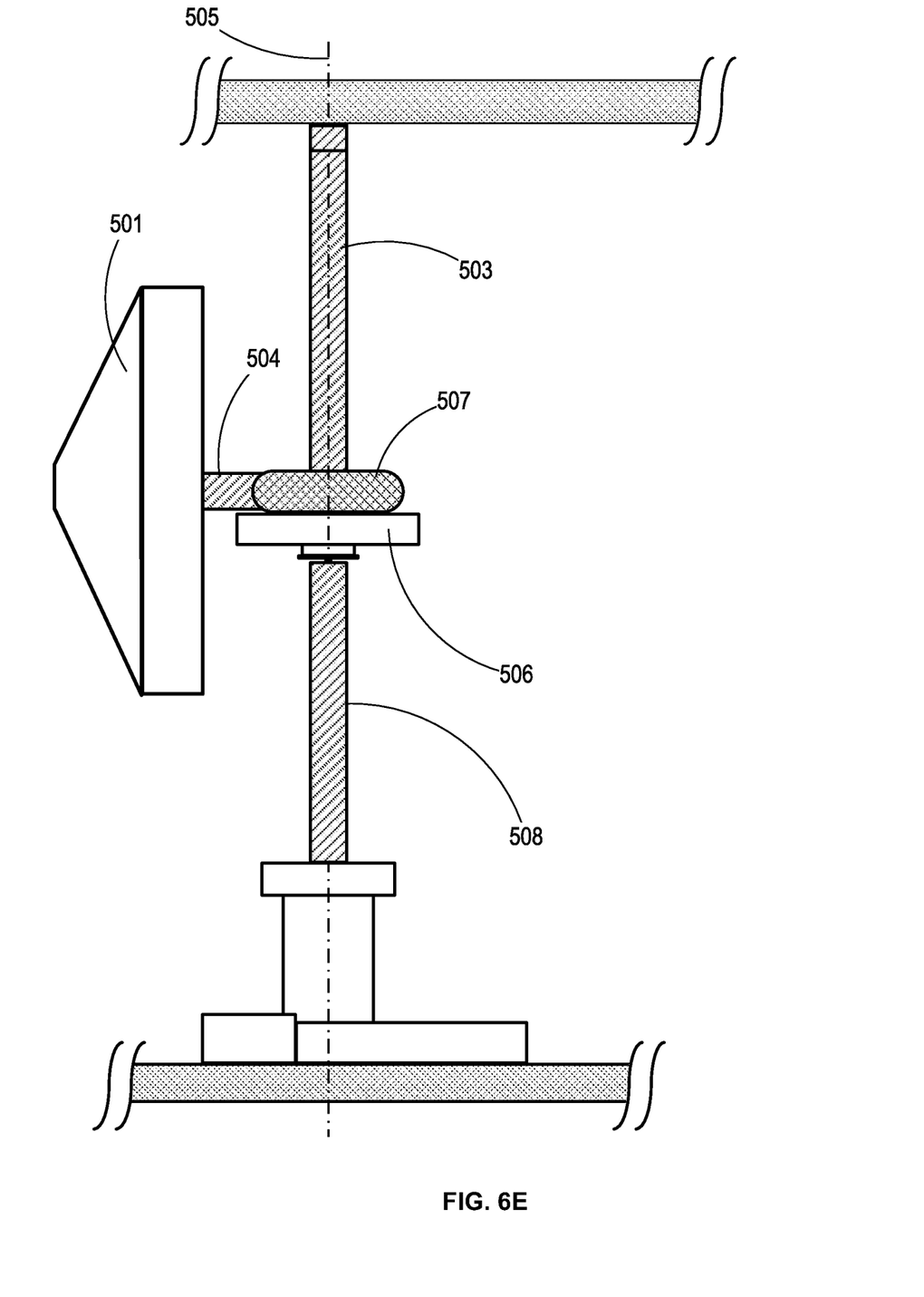
FIG. 6E illustrates the configuration of FIG. 6A as arranged with the conical magnet oriented to the left of the SUI, according to an embodiment of the invention.

FIG. 6E illustrates magnet 501 with the support mounting and orienting apparatus of FIG. 5A in conjunction with SUI stage 506 and support and positioning apparatus of FIG. 5B, with conical magnet 501 oriented to the left of the SUI, according to an embodiment of the invention.

Figure 6F:
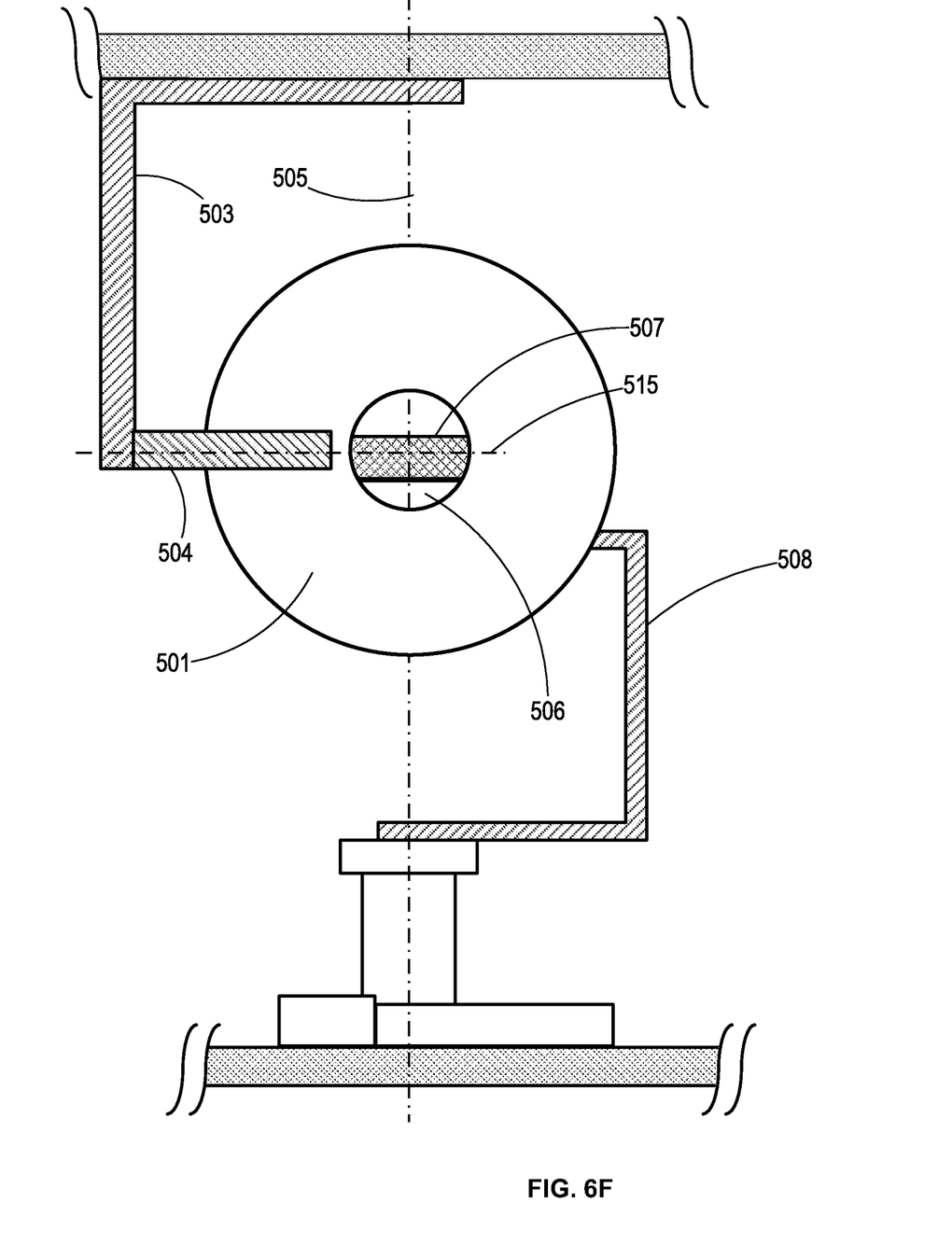
FIG. 6F illustrates the configuration of FIG. 6A as arranged with the conical magnet oriented in front of the SUI, according to an embodiment of the invention.

FIG. 6F illustrates magnet 501 with the support mounting and orienting apparatus of FIG. 5A in conjunction with SUI stage 506 and support and positioning apparatus of FIG. 5B, with conical magnet 501 oriented in front of the SUI, according to an embodiment of the invention. Compare with FIG. 6C, as described above, in light of the remarks above concerning multiple configurations for achieving the same orientation of magnet 501.

Figure 6G:
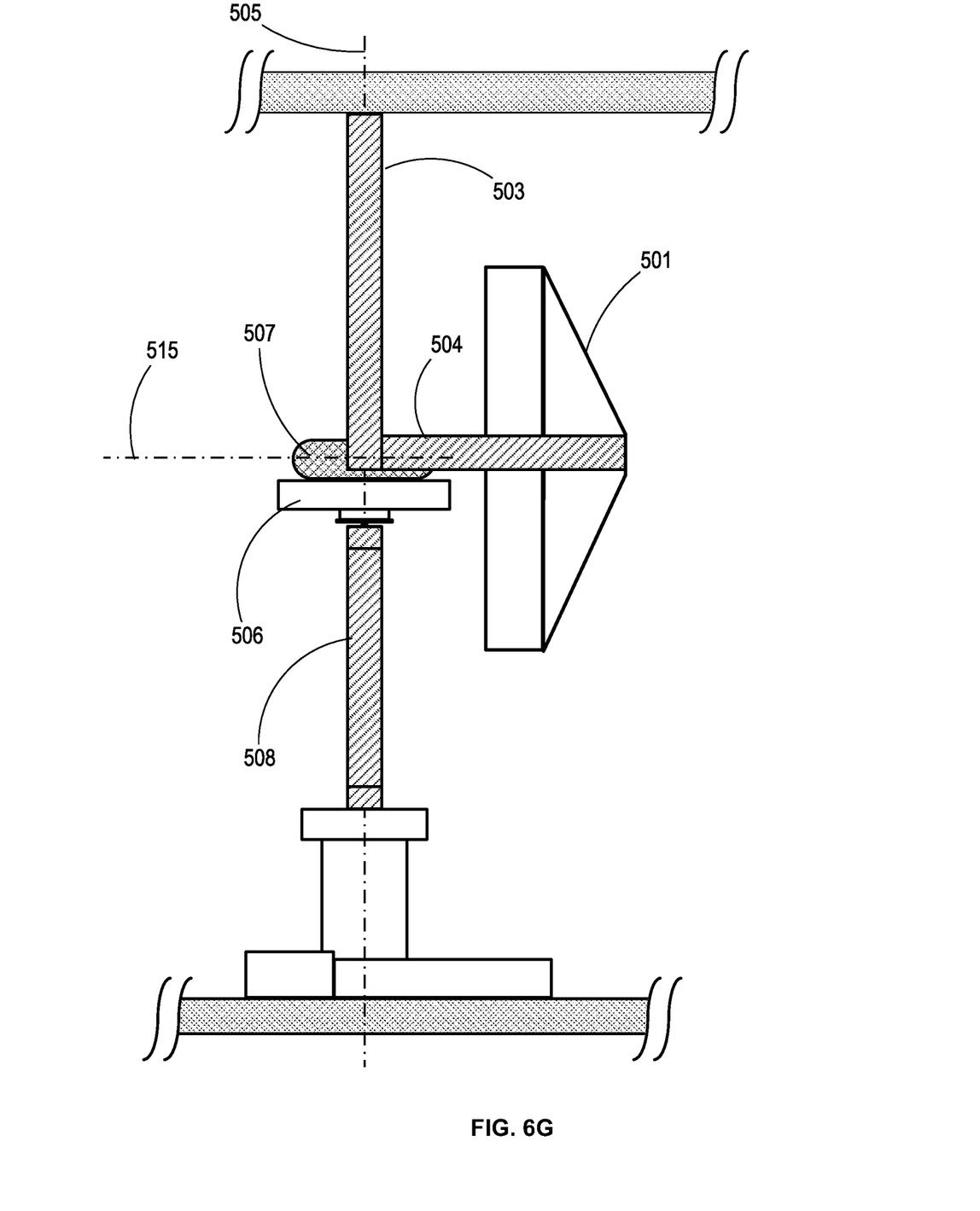
FIG. 6G illustrates the configuration of FIG. 6A as arranged with the conical magnet oriented to the right of the SUI, according to an embodiment of the invention.

FIG. 6G illustrates magnet 501 with the support mounting and orienting apparatus of FIG. 5A in conjunction with SUI stage 506 and support and positioning apparatus of FIG. 5B, with conical magnet 501 oriented to the right of the SUI, according to an embodiment of the invention.

What is claimed is:

1. A system for creating and controlling a magnetic field to manipulate a miniaturized mobile device with a magnetic component in a medium, the system comprising: a cylindrical organization of a plurality of rod-shaped magnets enclosing a hollow space for a specimen, each of said magnets extending along an axis and having a diametral magnetization;
wherein the plurality of magnets comprises: a first array of magnets forming a first Halbach array, and a second array of magnets forming a second Halbach array, wherein the magnets of the first Halbach array and the magnets of the second Halbach array are interleaved in an alternating fashion such that magnets of the first Halbach array always have magnets of the second Halbach array as their nearest neighbors; and
a motor drive operative to:
simultaneously rotate all the magnets of the first array about their respective axes; and simultaneously rotate all the magnets of the second array about their respective axes; and
wherein the rotation of the magnets of the first array is independent of the rotation of the magnets of the second array, and
wherein the manipulation of the device with the magnetic component is propulsion of the device within the specimen and/or expulsion of a payload from the device into the specimen.

* * * * *